United States Patent [19]

Harnsberger

[11] 4,280,981

[45] Jul. 28, 1981

[54] BLOOD OXYGENATOR

[75] Inventor: Frederick D. Harnsberger, Irvine, Calif.

[73] Assignee: C. R. Bard, Inc., Murray Hill, N.J.

[21] Appl. No.: 91,771

[22] Filed: Nov. 6, 1979

[51] Int. Cl.³ .............................................. A61M 1/03
[52] U.S. Cl. ......................................... 422/46; 422/47
[58] Field of Search ................... 422/46, 47, 45, 201; 261/122, 124, DIG. 28; 55/255, 256; 128/DIG. 3

[56] References Cited

U.S. PATENT DOCUMENTS

| 3,112,793 | 12/1963 | Sass | 165/177 X |
|---|---|---|---|
| 3,768,977 | 10/1973 | Brumfield et al. | 422/46 |
| 3,769,162 | 10/1973 | Brumfield | 422/46 X |
| 3,769,163 | 10/1973 | Brumfield | 422/45 X |
| 3,770,384 | 11/1973 | Brumfield | 422/47 |
| 3,807,958 | 4/1974 | Brumfield | 422/46 |
| 3,964,873 | 6/1976 | Aramaki et al. | 422/201 |
| 4,014,962 | 3/1977 | del Notario | 165/177 X |
| 4,138,464 | 2/1979 | Lewin | 422/46 |

Primary Examiner—Barry Richman
Attorney, Agent, or Firm—Richard H. Zaitlen

[57] ABSTRACT

An improved blood oxygenator including a first chamber having a plurality of oxygenator tubes disposed therein with each tube having an elongated cross-section. A blood inlet for introducing blood and a oxygen inlet for introducing oxygen gas into the blood are located on the oxygenator such that a mixture of blood and oxygen flows through the tubes where the blood is oxygenated. A blood foam exits from the tubes and then flows through a ring of reticulated polyurethane causing the blood to be further oxygenated. A defoamer is disposed about the first chamber and defoams the blood. The blood is then filtered and collected in a reservoir and can be withdrawn from the oxygenator through a blood outlet port.

19 Claims, 10 Drawing Figures

BLOOD OXYGENATOR

BACKGROUND OF THE INVENTION

1. Field of the Invention

This invention relates to an improved blood oxygenator, and more specifically, to an oxygenator having a plurality of uniquely configured oxygenator tubes.

2. Prior Art

Blood oxygenators are well recognized in the prior art. In such devices, the oxygenator functions so as to enable oxygen gas to contact blood such that the oxygen reacts with the hemoglobin in the blood with the resultant absorption of the oxygen into the blood and the release of carbon dioxide therefrom. Examples of such prior art oxygenators are disclosed in U.S. Pat. Nos. 3,768,977; 3,769,162; 3,769,163; 4,067,696; and 3,547,591. Other examples of oxygenators are those sold by William Harvey Research Corporation under the designations "Hybrid Disposable Oxygenator Model H-1000 and Model H-1100". With respect to the two Harvey units, multiple, small diameter oxygenator tubes are provided in a patterned parallel array. A base header plate secures the patterned array of oxygenator tubes at the bottom thereof, and a top header plate secures the oxygenator tubes at the top thereof. A tubular boundary case surrounds and secures the base header plate, the top header plate and the multiple oxygenator tubes in a specific configuration. Heat transfer fluid conduits are disposed through the boundary case such that heat transfer fluid can flow into and out of the case heating the tubes, but without any mixing of the blood and heat transfer fluid.

In the operation of the Harvey devices, a two-phase blood-oxygen gas mixture circulates upward through the multiple oxygenator tubes and a temperature controlled heat transfer fluid circulates exterior to the tubes through the tubular boundary case. The two-phase blood-oxygen flow in the oxygenator is formed with a minimum of turbulence and damage to the blood by providing a specifically configured blood-oxygen manifold. The manifold includes a blood manifold and an oxygen manifold configured such that a plurality of oxygen bubbles are readily infused into the blood as it flows through the oxygenator. The case is circumferentially surrounded by a diffusor made of reticulated polyurethane foam which further oxygenates the blood as it exits out of the tubular boundary case. An outer defoamer layer of treated polyurethane is circumferentially disposed about the tubular case and the diffusor such that when the blood foam contacts such defoamer the blood foam bubbles collapse.

While such units have been found to be useful in the extra-corporeal treatment of blood, a number of shortcomings are believed to exist. One is the fact that as the blood is introduced into the oxygenator, some of the tubes are thought to permit more blood to flow therethrough than others. This is believed to be due to the creation of varying pressures adjacent the bottom of the tubes. Because of this problem, care must be exercised to insure that the blood is being sufficiently oxygenated. Usually, more oxygen is pumped through the blood than may otherwise be necessary to compensate for any flow irregularities. The problem is that the contact between by the oxygen on the blood is believed to cause hemolysis, i.e. a breakdown of the red blood cells.

The present invention is directed to an oxygenator which incorporates uniquely configured oxygenator tubes. These tubes are specifically arranged and configured such that problems of varying flow rates through different oxygenation tubes is substantially overcome. In addition, because the efficiency of each tube is greater than in prior Harvey units, the number of tubes necessary can be decreased. By the use of the oxygenator of the present invention, improvements in heat exchange, oxygen transfer rate and dynamic priming volume can be achieved. Other advantages of the oxygenator of the present invention are discussed in greater detail hereinbelow.

SUMMARY OF THE INVENTION

In the blood oxygenator of the present invention, a first chamber is provided which has a plurality of elongated, generally elliptical oxygenator tubes disposed therein. Blood flows into the tubes adjacent the bottom thereof and out the top. A base header plate and a top header plate are joined to the chamber and secure the tubes in a predetermined pattern. Means for introducing a heat transfer fluid into the first chamber and removing the same therefrom enables the temperature of the blood to be regulated. A manifold introduces a mixture of oxygen bubbles and blood into the oxygenator tubes. The manifold is joined to the first chamber adjacent to the base header plate such that the blood and oxygen mixture flows through the tubes where the blood is oxygenated. The blood exits from the tubes adjacent the top header plate in the form of a blood foam. A polyurethane ring which encourages the further oxygenation of the blood is disposed adjacent the top header plate. The ring is preferably sandwiched between the first chamber and a downcomer or flow guide member which is joined to the first chamber adjacent the top header plate. The flow guide member directs substantially all of the blood foam through the polyurethane ring.

A tubular section of defoamer material is circumferentially disposed about the first chamber such that the blood foam contacts the defoamer after it has flowed through the polyurethane ring. When the blood foam contacts the defoamer, the bubbles collapse such that a stream of defoamed blood is produced. The blood then flows into a reservoir located exterior to the first chamber. A blood outlet port is provided on the reservoir which enables the now-oxygenated and defoamed blood to be readily removed from the oxygenator.

The novel features which are believed to be characteristic of the invention, both as to its organization and method of operation, together with further objectives and advantages thereof will be better understood from the following description considered in connection with the accompanying drawings in which a presently preferred embodiment of the invention is illustrated by way of example. It is to be expressly understood, however, that the drawings are for the purpose of illustration and description only and are not intended as a definition of the limits of the invention.

DESCRIPTION OF THE PREFERRED EMBODIMENT

Figure 1:
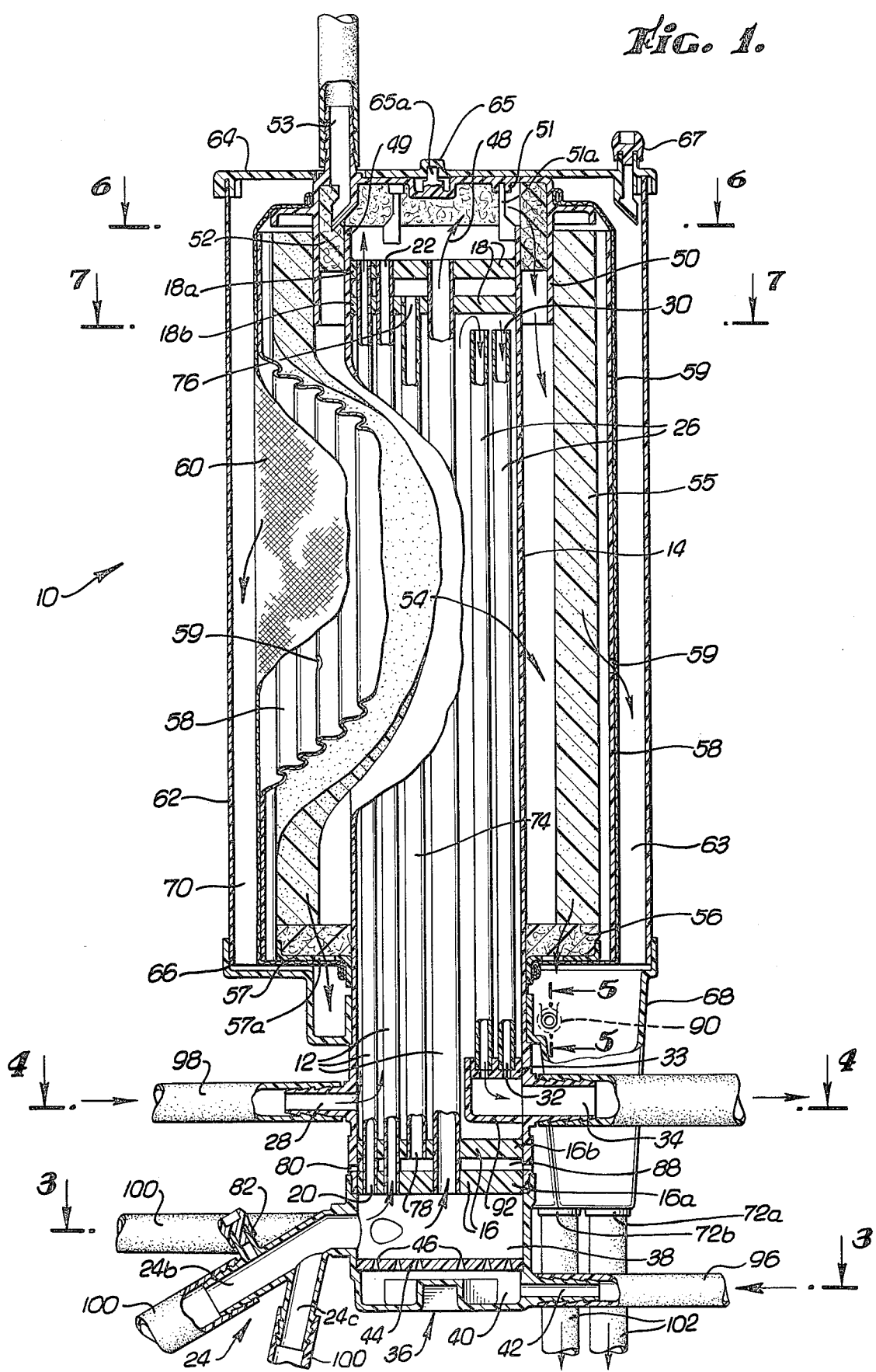
FIG. 1 is partial sectional view of the blood oxygenator of the present invention.

In the preferred embodiment of the present invention, the blood oxygenator 10 as shown in FIG. 1 includes a plurality of elongated, aluminum oxygenator tubes 12 which are disposed in a first plastic tubular chamber 14. Blood and oxygen gas are introduced at the bottom of chamber 14, with the blood and oxygen mixture flowing through the various tubes 12. The blood and oxygen mixture flows through tubes 12 so as to fill each of the tubes and to thoroughly mix. As a result of mixing, carbon dioxide is removed from the blood and the blood is saturated with oxygen. Arterialized blood and blood foam flow out of the top of chamber 14 and is subsequently defoamed. The defoaming step collapses the bubbles of the blood such that the entrapped undissolved gases escape therefrom. The arterialized blood is then collected in the oxygenator 10 such that it can then be withdrawn and returned to a patient.

Although all aspects of the blood oxygenator 10 of the present invention are not presently completely understood, it is believed that a number of advantages over similar prior art devices are achieved by the shape, location and quantity of the oxygenator tubes 12. Because tubes 12 have an elongated or oblong cross-section, a thinner film of blood is passed through each tube 12 than would be the case if a generally cylindrical tube were used. Also, a larger surface area for the same volume of blood is provided than would be the case if round tubes were used. The elongated cross-section of tubes 12 and the thinner film of blood enables heat transfer to more readily occur between the blood and a heat transfer fluid flowing about the various tubes 12. In addition, the larger surface area per internal volume of blood also effects the gas transfer rate. The configuration of tubes 12 also enable the blood to be more readily oxygenated. While not to be bound by any theory, it is believed that improved oxygenation is because a larger portion of blood volume forms a film on the internal surface of tubes 12 and thus more blood is exposed to the oxygen gas.

The tubes 12 of the oxygenator 10 are also arranged so as to substantially overcome problems of poor flow rates through some tubes associated with prior art units. This enables the oxygenator 10 to use fewer tubes than in many prior art units. Fewer tubes means that less blood is contained inside the oxygenator 10 during operation.

Referring again to FIG. 1, one can see that oxygenator tubes 12 are arranged in a patterned, parallel and generally annular configuration. Tubes 12 are retained in this specific configuration by mounting them between base header plates 16 and top header plates 18. In turn, header plates 16 and 18 are joined to the chamber 14 adjacent the top and bottom thereof so as to close off the interior of chamber 14. Each of the oxygenator tubes 12 has an inlet 20 and an outlet 22. Inlet 20 extends through the base header plates 16 so as to be in flow communication with the incoming blood and oxygen as hereinbelow described. The outlet 22 of each tube 12 extends through the top header plates 18 such that the blood and oxygen can readily flow into and out of tubes 12 and through chamber 14.

A series of heat transfer fluid tubes 26 are also disposed in chamber 14. A heat transfer fluid, usually water, enters chamber 14 through inlet port 28 and flows about each of the tubes 12. In this manner, the temperature of the blood is regulated. As the fluid continues to flow up toward top header plates 18, it reaches the top inlets 30 of fluid tubes 26. The heat transfer fluid then flows down the various tubes 26 and out the bottom outlets 32. In the preferred embodiment, tubes 26 are held in place by plate 33 and outlet guide 92. From outlets 32, the water is directed out of chamber 14 through heat transfer fluid outlet port 34.

Joined to the first tubular chamber 14 adjacent base header plates 16 is a blood-oxygen mixing manifold 36. Manifold 36 is comprised of an upper blood manifold 38 and a lower oxygen manifold 40. An oxygen inlet port 42 is in flow communication with the oxygen manifold 40 such that oxygen gas can readily flow through port 42 into the manifold 40. A generally circular plate 44 is located between blood manifold 38 and oxygen manifold 40 and has a plurality of openings or gas inlet orifices 46. These orifices 46 are arranged and configured such that a multiplicity of finely divided oxygen bubbles are created as the oxygen flows through plate 44 into the blood manifold 38. In turn, blood flows into blood manifold 38 through blood inlet port 24 where it mixes with the oxygen bubbles.

The bubbles of oxygen encourage the blood up through the inlets 20 of the various oxygenator tubes 12 where oxygenation of the blood occurs. When the blood reaches the outlets 22 of each of the oxygenator tubes 12, it flows out therefrom in the form of a blood foam generally indicated by arrow 48. A dam 49 extends upwardly from chamber 14 adjacent the top header plates 18. As the blood foam continues to flow out of outlets 22, it overflows the dam 49 and is directed through a rigorous mixing path created by an annular ring 52 of reticulated polyurethane foam. This flow is directed by a downcomer or flow guide member 50 which circumferentially surrounds the foam ring 52 and is joined to the chamber 14 adjacent the top header plates 18. In the preferred embodiment, coupling members 51, formed on guide member 50 mate with upwardly extending pin member 51a located on the chamber 14 adjacent the top thereof. Because the blood is forced to flow through the rigorous mixing path created by the annular foam ring 52, further interaction between the oxygen and blood takes place, thus further oxygenating the blood.

After the blood has passed through the foam ring 52, it flows into a defoamer 54. Defoamer 54 is preferably made of a reticulated polyurethane foam which has been treated with a silicone compound. This compound has been found to cause the blood foam to collapse so as to produce a defoamed blood. In the preferred embodiment, defoamer 54 is formed from a generally cylindrical section 55 of silicone-treated polyurethane foam circumferentially disposed about the first tubular chamber 14, and an annular bottom ring section 56 made of the same treated material. Defoamer section 55 is held in place by a corrugated shield or support member 58 which is likewise tubular and which circumferentially surrounds the defoamer section 55. Support member 58 has a plurality of openings 59 which permit some of the blood to flow outwardly through defoamer section 55 and support member 58. To insure that all the blood comes in contact with at least some portion of the defoamer material, ring section 56 of defoamer material is disposed adjacent the bottom of defoamer section 55. Defoamer section 56 is positioned on an outwardly extending shelf 57 having a plurality of openings 57a disposed therethrough. Openings 57a also permit blood to flow out of the defoamer 54.

As the blood flows through the defoamer 54, it eventually comes in contact with a nylon tricot filter 60 which filters the defoamed blood. Filter 60, in the preferred embodiment, circumferentially surrounds the support member 58 as well as defoamer sections 55 and 56. In this manner all of the blood is filtered before it flows out of the oxygenator 10. To contain the filtered and defoamed blood in the oxygenator 10, a second chamber 62 is circumferentially disposed about the filter 60, corrugated member 58 and defoamer 54, and is held in place between a top closure member 64 and a bottom closure member 66.

Top closure member 64 has a centrally located coupling member 65 which mates with a pin member 65a formed on guide member 50. This helps insure a more rigid and stable configuration. Depending from bottom closure member 66 and in flow communication with the space between chamber 14 and of chamber 62 is a blood tank 68. Tank 68, along with closure member 66 and chamber 62, forms a blood reservoir 70 which holds the defoamed and filtered blood prior to use. Tank 68 includes blood outlet ports 72 such that the blood can be easily withdrawn from oxygenator 10 and delivered to a patient or to another end use.

Figure 2:
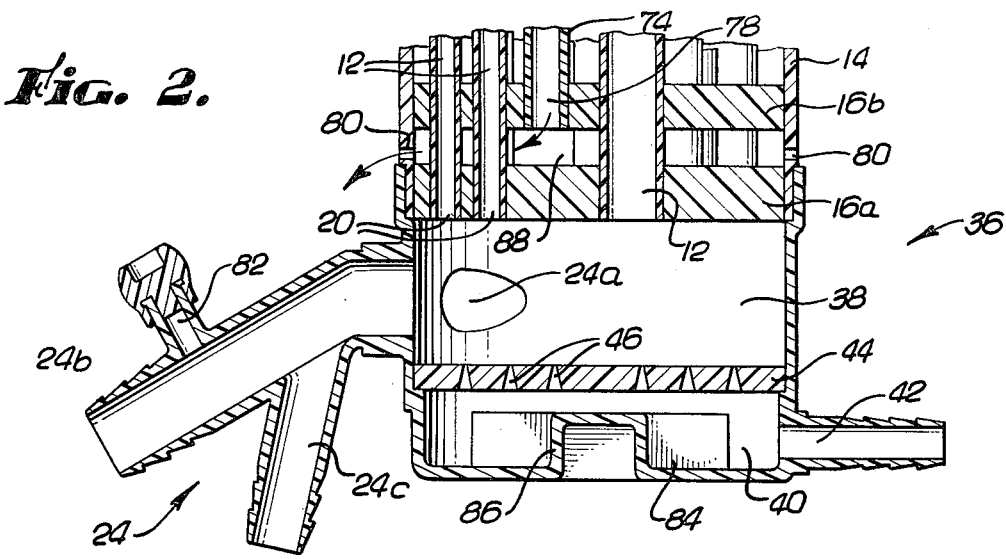
FIG. 2 is an enlarged cross-sectional view of the blood-oxygen mixing manifold.
Figure 3:
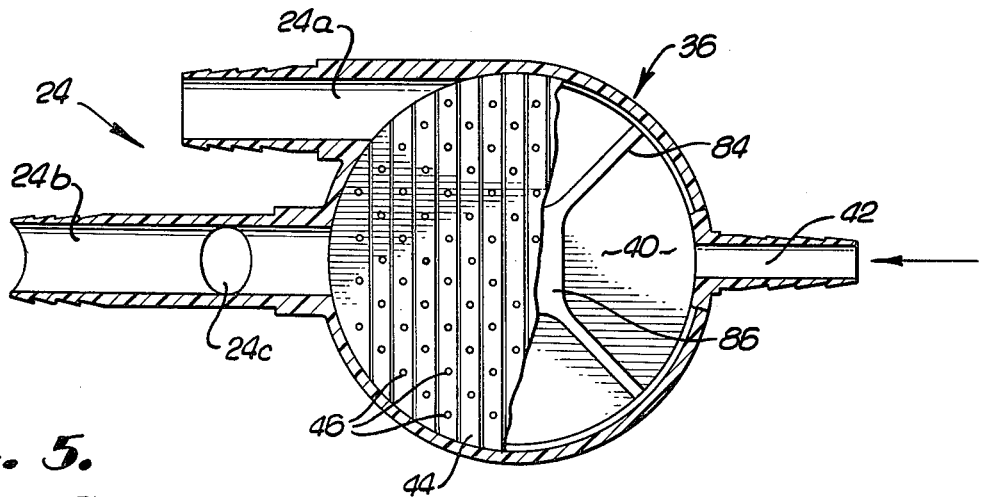
FIG. 3 is a cross-sectional view of FIG. 1 taken along lines 3—3 and showing the blood manifold.

Referring now to FIGS. 2 and 3, the blood-oxygen mixing manifold 36 is more clearly illustrated. Manifold 36 is comprised of a blood manifold 38 and oxygen manifold 40 arranged in a configuration, with oxygen manifold 40 disposed beneath blood manifold 38. Oxygen inlet port 42 communicates with the oxygen manifold 40 and directs oxygen into manifold 40. The oxygen flows out of manifold 40 through openings 46 formed in plate 44 such that finely divided oxygen bubbles are infused into the blood. Also located in manifold 40 are a plurality of radially positioned support rib members 84 which terminate in a centrally located rectangular section 86.

Blood manifold 38 includes a blood inlet port generally identified as numeral 24. In the preferred embodiment, a number of blood inlet ports 24a, 24b and 24c are provided. Preferably, patient inlet port 24b is the main extracorporeal circuit entrance to the oxygenator 10 where oxygenpoor blood enters the oxygenator 10. Ports 24a and 24c permit additional blood to flow into the blood manifold 38 when such is desired. Note that on inlet port 24b, access port 82 is provided which enables a sample of the blood to be obtained as the blood is flowing into manifold 38. As the blood and oxygen mix in blood manifold 38, some degree of oxygenation may occur. However, in order to sufficiently oxygenate the blood, the blood is directed up through oxygenator tubes 12 where oxygenation of the blood takes place.

Referring again to FIG. 1, a safety feature of the present invention is illustrated. As previously discussed, water, the preferred heat transfer fluid, flows up chamber 14 in contact with the various oxygenator tubes 12. The blood oxygenator tubes 12 extend through top header plate 18a as well as bottom header plate 16a. Should water somehow find its way past header plate 18b, overflow tube 74 would direct such water through the top opening 76 in tube 74 to the outlet 78 thereof. As shown in FIGS. 1 and 2, such outlet 78 communicates with space 88 formed between bottom header plates 16a and 16b. Likewise, should water leak past bottom header plate 16b, it would also flow into space 88. Thus, should a water leak occur adjacent the top or bottom of chamber 14, the water would be directed to space 88 and then to the exterior of the oxygenator 10 through escape ports 80.

Figure 4:
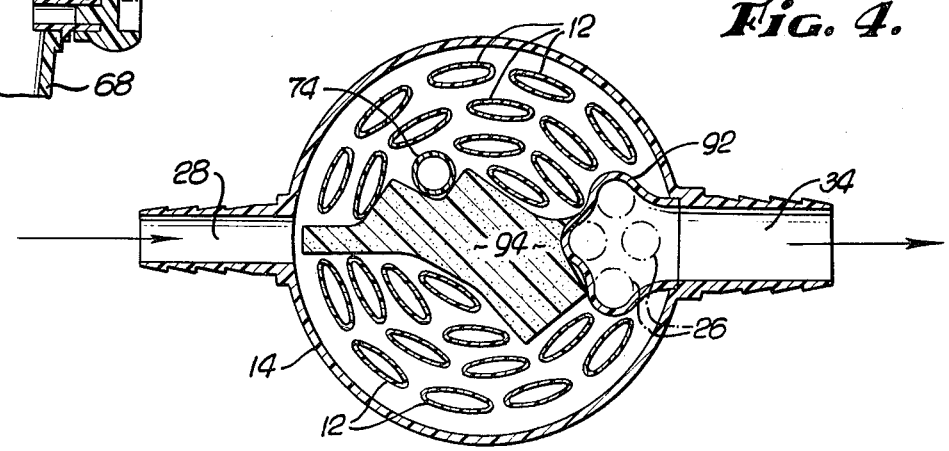
FIG. 4 is a cross-sectional view of FIG. 1 taken along lines 4—4 and showing the outlet ends of the various oxygenator tubes of the present invention.

Referring now to FIGS. 1 and 4, the oxygenator tubes 12 are illustrated. In the preferred embodiment, each oxygenator tube 12 has a generally elliptical cross-section. The tubes 12 are arranged and configured in chamber 14 in a generally radial, outwardly extending annular configuration, with their elongated axes generally perpendicular to the radius of the chamber 14. While FIG. 4 does indicate that the annular array of tubes 12 is somewhat interrupted by return tubes 26 and spacer member 94, such pattern is still considered to be generally annular in cross-section.

As discussed hereinabove, it was believed that one problem with prior art oxygenators was that there were oxygenator tubes located over pressure zones which were not conducive to blood flowing therethrough. In the present invention, the tubes 12 are located over pressure zones more conducive to blood flow. More specifically, it was determined that due to flow dynamics, the pressure adjacent the center of the bottom plate in prior art units interferred with the blood flowing through the oxygenator tubes located in the center of the oxygenator chamber. In the preferred embodiment of oxygenator 10, there are no oxygenator tubes 12 adjacent the center, i.e. along the axis of chamber 14. In order to prevent the absence of tubes 12 in this area of chamber 14 from acting as a flow channel for the heat transfer fluid, centrally located elongated polystyrene spacer member 94 extends from a point adjacent the bottom of the chamber 14 to the top thereof.

Figure 6:
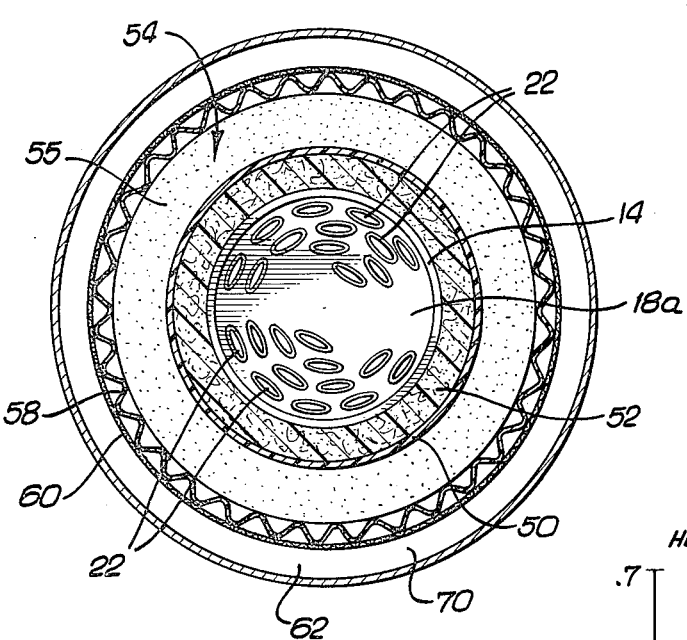
FIG. 6 is a cross-sectional internal view of FIG. 1 taken along lines 6—6 and showing some of the various members through which the blood flows in the oxygenator of the present invention.
Figure 7:
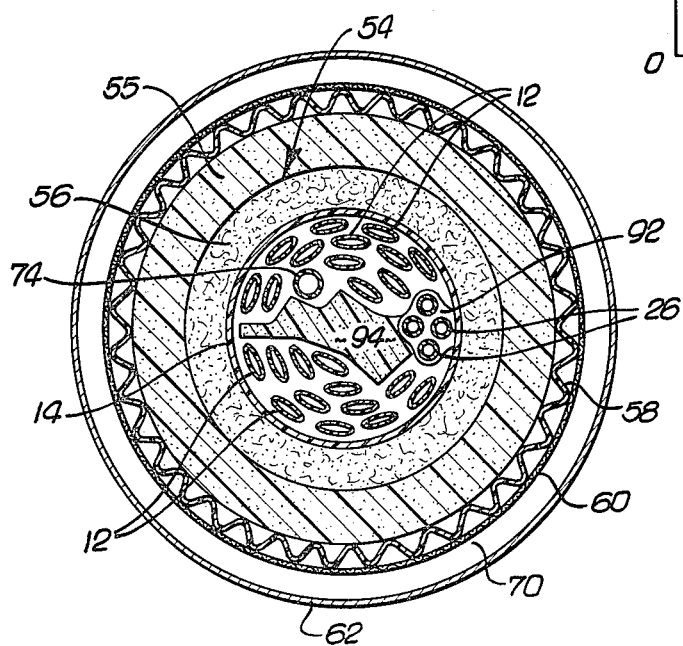
FIG. 7 is a cross-sectional view of FIG. 1 taken along lines 7—7 also showing some of the various internal members of the oxygenator of the present invention.

Referring now to FIGS. 1, 6 and 7, one can see that first tubular chamber 14 is axially located in the center of the oxygenator 10. Chamber 14 is circumferentially surrounded by reticulated polyurethane foam ring 52. Ring 52, as discussed above, forces the blood foam to flow along a rigorous mixing path thereby further encouraging the oxygenation of the blood. Surrounding foam ring 52 is flow guide member 50. Member 50 not only retains the foam ring 52 in a specific position, but helps direct the blood through ring 52 and into the defoamer 54. Defoamer 54, in the preferred embodiment, is comprised of a tubular section 55 of silicone-treated polyurethane foam and annular section 56. Sections 55 and 56 are positioned in the oxygenator 10 such that all the blood must pass therethrough before flowing out of the oxygenator 10. Surrounding defoamer section 55 is a corrugated member 58 which has a plurality of openings 59 disposed therethrough. Member 58 is corrugated to aid in encouraging the blood after it has been defoamed to flow through openings 59 and toward the bottom of the oxygenator 10.

Surrounding corrugated member 58 is a nylon filter 60. Filter 60 insures that any undesirable material which has not been previously removed is substantially precluded from flowing therethrough. In this manner it is hoped that the blood which ultimately is delivered to the patient is free of all gross impurities, blood embuli and the like. Circumferentially surrounding all the previously mentioned elements is an exterior chamber 62. Chamber 62 forms the exterior wall of the blood reservoir 70.

Figure 5:
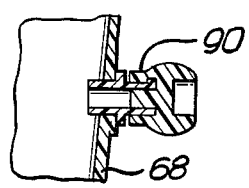
FIG. 5 is a cross-sectional view of FIG. 1 taken along lines 5—5 and showing a port on the blood reservoir tank.

As is common in many oxygenators and other medical devices, the oxygenator 10 of the present invention includes a number of access ports for obtaining samples or adding fluid. An example is illustrated in FIG. 5 as access port 90 formed on tank 68. Other access ports are found on the top closure 64, access port 65, and on one of the blood inlet ports 24b, access port 82.

Figure 8:
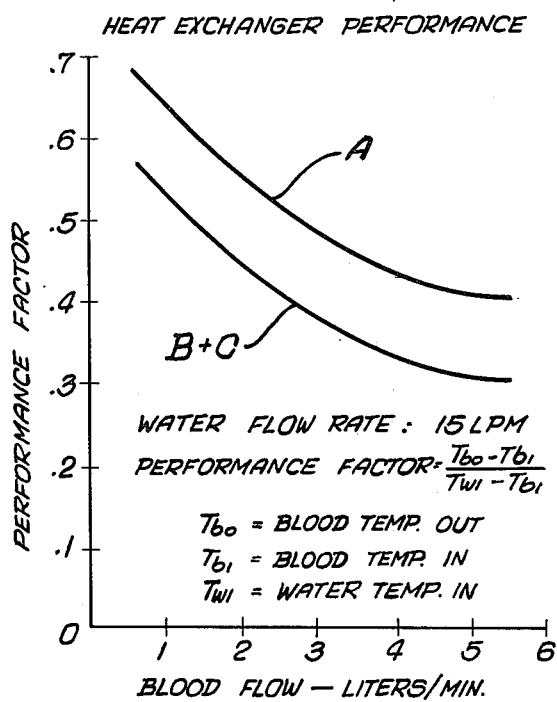
FIG. 8 is a graph illustrating the heat exchange performance factor vs. blood flow for the oxygenator of the present invention and prior art devices.

Referring now to the graph shown in FIG. 8, one of the distinct improvements and advantages of the oxygenator 10 of the present invention as compared with the prior art is illustrated. In FIG. 8, the heat exchange performance factor (as defined in the graph) of various blood oxygenators is plotted against the blood flow. More specifically, line A represents the performance factor versus blood flow for the oxygenator 10 of the present invention. Lines B and C are representative of the Harvey Models H-1000 and H-1100 which are round tube type oxygenators. The graph represents various gas and blood flow conditions and the results indicate a 10 to 33% increase in the heat exchange performance coefficient ($C_p$) for the configuration of the present invention over the configuration of these prior art Harvey devices.

It is understood that heat exchange performance coefficient ($C_p$) is defined herein as:

$$C_p = (T_{Bo} - T_{Bi})/(T_{wi} - T_{Bi})$$

Figure 9:
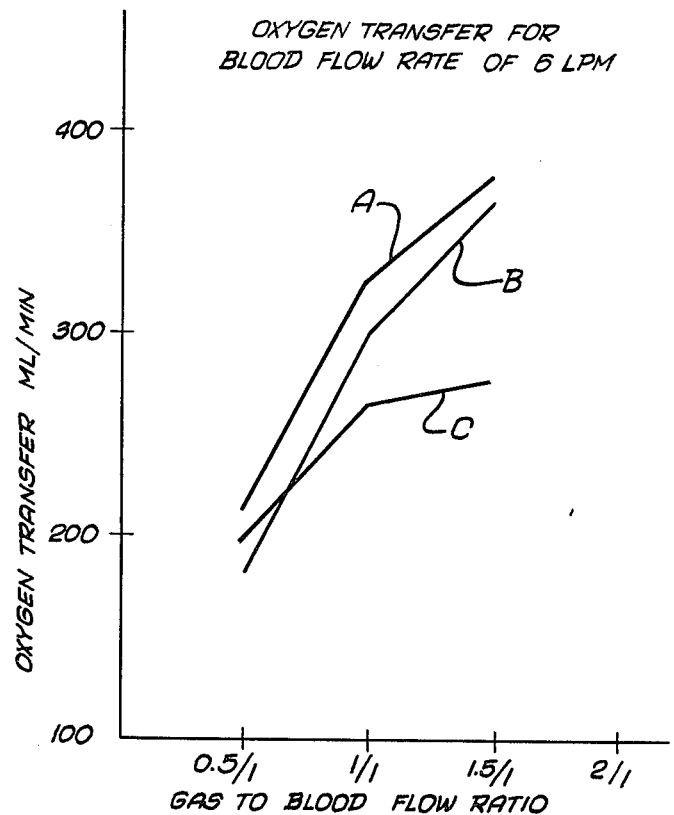
FIG. 9 is a graph illustrating the oxygen transfer vs. gas-to-blood flow ratio for the device of the present invention and prior art devices.

Where:
$T_{Bo}$ = Temperature blood out
$T_{wi}$ = Temperature water in
$T_{Bi}$ = Temperature blood in Referring now to the graph shown in FIG. 9, the oxygen transfer of various oxygenators has been plotted against the gas to blood flow ratio. Oxygen transfer rates for the oxygenator 10 of the present invention are shown as line A. Line B represents the oxygen transfer rate for the Harvey Model H-1100 and line C represents the oxygen transfer rate for the Harvey Model H-1000. It can be seen that the oxygen transfer rate for the oxygenator 10 of the present invention, line A, is up to about 30% higher than the rate for the H-1000, line C, under similar conditions. The rates for the H-1100, line B, and the oxygenator 10 of the present invention are much closer together. From this one can conclude that the major portion of the improvement in oxygen transfer performance of oxygenator 10 is attributable to the change in the location of the defoamer assemblies. (The H-1000 has a different defoamer configuration than the H-1100 and H-1500). The improvements in the oxygenator 10 of the present invention compared with the H-1100 is believed to be attributable to the larger effective circumference (larger surface area per internal volume) of the tubes 12 compared with the round tubes used in the H-1100.

Figure 10:
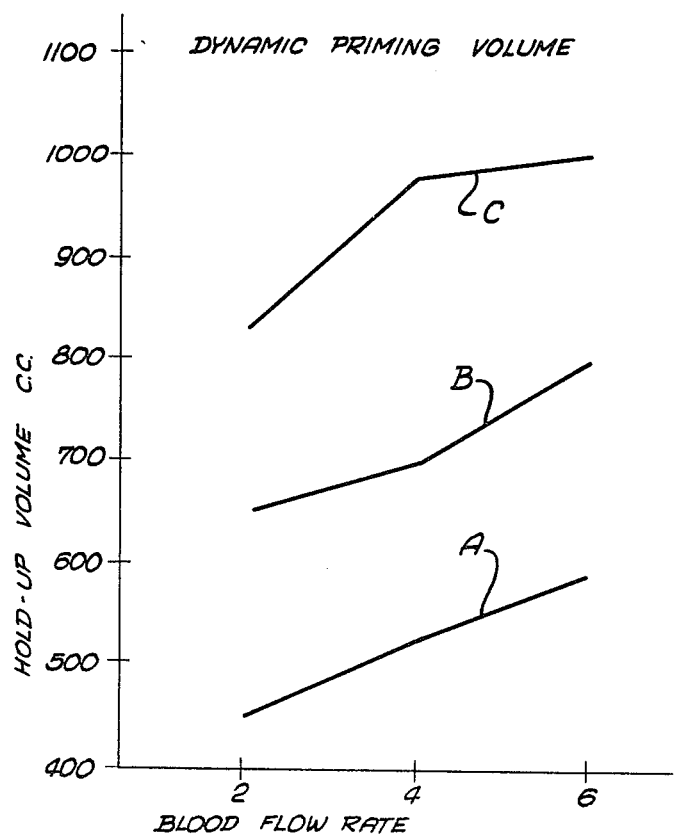
FIG. 10 is a graph illustrating the dynamic priming volume vs. blood flow rate of the device of the present invention and prior art devices.

Referring now to the graph shown in FIG. 10, the hold up volume has been plotted against the blood flow rate for the oxygenator 10 and similar Harvey units. One can see that for the oxygenator 10, shown by line A, the dynamic priming volume is substantially less than that of the H-1100 unit, line B or the H-1000 unit, line C. As used herein, dynamic priming volume is a measurement of the volume of blood contained in the oxygenator (not including reservoir volumes) during operation. The reduction of the dynamic priming volume of oxygenator 10 as compared to these other units is believed attributable to (i) the changes in the defoamer assemblies mentioned above, and (ii) the reduction in the number of tubes which eliminates one-third of oxygenator tubing volume. This reduced tubing volume in the oxygenator 10 of the present invention does not adversely impact the blood flow rate per tube, venous inlet pressure or related performance characteristics as the tube volume reduction involves the elimination of less efficient tubes. In the oxygenator 10 of the present invention, preferably 24 oxygenator tubes are used. In prior Harvey units, 32 oxygenator tubes were used.

OPERATION OF THE DEVICE

In operating the blood oxygenator 10 of the present invention, initially the oxygenator 10 is positioned in an associated mounting bracket (not shown). Various flexible conduits are joined to the associated inlet and outlet ports such that blood, oxygen and water can flow through the oxygenator 10. Preferably, oxygen tubing 96 is first joined to the oxygen inlet port 42 and oxygen is permitted to flow into the oxygenator 10 at the rate of approximately 2 LPM. It should be understood that while in the preferred embodiment oxygen gas is used, other gases and mixtures of gases are also within the scope of the present invention. Heat transfer fluid tubing 98 is then joined to the fluid inlet port 28 and to the fluid outlet port 34. Various blood tubing 100 is then joined to the oxygenator 10. More specifically, tubing 100 is joined to the cardiotomy inlet 24c and the venous inlet 24b. Likewise, tubing 102 is also joined to the blood outlet ports 72, and more specifically, to coronary perfusion outlet 72a and to arterial outlet 72b. Although not shown, the device 10 is preferably equipped with various temperature probes which are inserted into the blood tank 68 and at one other location. In this manner, the temperature of the blood as it flows through the oxygenator 10 can be readily determined.

Before operating the oxygenator 10 of the present invention, it is necessary to prime the unit with blood. Such initial priming can be introduced into the oxygenator 10 through port 53. If desired, additional blood can also be added for through access port 67 found on the top closure member 64.

As blood begins to flow through port 24 into blood manifold 38, oxygen, which is flowing up through the oxygen manifold 40 through the plurality of openings 46 in plate 44, mixes with the blood in the blood manifold 38 and causes the blood to flow in a generally upward direction through the plurality of oxygenator tubes 12.

While a wide variety of other generally elongated configurations are within the scope of the present invention for the cross-section of tubes 12, it has been determined that an elliptical configuration has less tendency to collapse as a result of external pressure and is more easily fabricated, and thus is preferred. Wall strength is especially important inasmuch as the water pressure in chamber 14 can be approximately 60 psi. Furthermore, the chamber 14 is test pressurized to 90 psi.

It has also been determined that the temperature of the blood should be regulated. To achieve this end, water, or another heat transfer fluid flows into chamber 14, through port 28 and up toward top header plates 18. As the water flows through chamber 14, and around spacer 94, desirable flow patterns and consequently good heat transfer with the tubes 12 is achieved. Further, because tubes 12 have an elongated, and preferably ellipitical, cross-section, more heat is exchanged between the tubes 12 and the blood than with round tubes. When the water reaches header plate 18b, it then flows down heat transfer fluid tubes 26 and out of the device 10 through outlet port 34. Should some water manage to flow by plate 18b, it would flow between top header plates 18a and 18b. An overflow tube 74 communicates with the space between the header plates 18a and 18b and directs water to space 88 formed between bottom header plates 16a and 16b. From here, the water would flow out the device 10 through a series of circumferentially formed ports 80. In this manner, water and blood flow are substantially precluded from mixing with each other.

As the blood continues to flow up through the various oxygenator tubes 12, it exits therefrom through outlets 22 in the form of a blood foam. The blood foam would then flow, as indicated by arrow 48, over the dam 49 and through the annular ring 52 of reticulated polyurethane foam. Ring 52 causes further mixing of the blood and oxygen and is believed to resize blood bubbles. This further mixing and bubble resizing causes further oxygenation of the blood. The flow of the blood foam through member 52 is directed by the flow guide member 50 which channels the foam through the ring 52.

As the blood foam flows through ring 52, it continues to flow generally downward and contacts the defoamer 54. Defoamer 54 is also made of reticulated polyurethane foam, but has a smaller pore size than ring 52 and is treated with a silicone composition which causes the blood bubbles to collapse. In the preferred embodiment, defoamer 54 is made up of sections 55 and 56 which are positioned such that substantially all blood foam comes in contact with one or both sectons.

Circumferentially surrounding defoamer section 55 is corrugated support member 58. Member 58 channels the defoamed blood in a generally downward direction towards the bottom of the oxygenator 10. Member 58 also includes a plurality of openings 59 disposed along the length thereof which permit some of the blood to flow outwardly therefrom. Blood foam which does not contact section 55 continues to flow down until section 56 is reached. Here, remaining blood foam flows through section 56, thereby causing the blood bubbles to callapse. The resulting defoamed blood then flows through openings 57a in member 57 and into reservoir 68.

Member 58, as well as defoamer 54, is surrounded by a nylon filter element 60. Thus, as the blood flows through defoamer sections 54 or 56, it is filtered through element 60 which removes gross embuli. As the blood flows through element 60, a pool of blood is formed in the downwardly extending blood tank 68. When tank 68 is full, additional blood collects between chamber 62 and the outwardly extending base or bottom closure 66. Blood is withdrawn from tank 68 as needed through outlet ports 72.

The blood oxygenator 10 also includes a venting means for venting excess oxygen and/or carbon dioxide. The venting means of the present invention is formed by gaps (not shown) between the second chamber 62 and the top closure member 64. These gaps permit excess gases to be vented from the oxygenator 10. It should be understood that other well recognized venting means are also within the scope of the present invention.

While this invention has been described in its preferred embodiments, it should be understood that words which have been used are words of description rather than of limitation and that changes within the purview of the appended claims may be made without departing from the true scope and spirit of the invention in its broader aspects. For example, a wide variety of plastic materials can be used in the construction of chambers 14 and 62, defoamer 54 and the like. Likewise, tubes 12 are preferably made of aluminum, but other good heat-conducting materials are likewise within the scope of the present invention. This invention, therefore, is not to be limited to the specific embodiments discussed hereinabove.

What is claimed is:

1. In a blood oxygenator having a first generally cylindrical chamber with a plurality of oxygenator tubes disposed therein in a predetermined configuration, a blood-oxygen manifold joined to said chamber and having a blood inlet and an oxygen inlet, said manifold configured such that a mixture of blood and oxygen is directed into said tubes adjacent one end thereof, and means for defoaming said mixture of blood and oxygen as it exits out the other end of said oxygenator tubes, the improvement comprising wherein each said oxygenator tube has a generally elliptical cross-section with the elongated axis of each said tube being generally perpendicular to the radius of said first chamber, and further wherein said tubes are positioned in said predetermined configuration in a generally annular array so as to define a central, open space extending from one end of said chamber to the other.

2. The oxygenator according to claim 1 further including an elongated spacer member disposed in said open space in said first chamber along the axis thereof.

3. A blood oxygenator comprising:
   a first chamber having a plurality of elongated oxygenator tubes disposed therein with each said tube having an elongated cross-section, said plurality of oxygenator tubes arranged in a predetermined, generally annular array so as to define a central open space extending from one end of said first chamber to the other end thereof;
   means disposed in said central open space for spacing and positioning said tubes;
   blood inlet means for introducing blood into said tubes;
   oxygen inlet means for introducing oxygen gas into said blood such that a mixture of blood and oxygen flows through inlet ends of said tubes, thereby oxygenating said blood and forming a blood foam as the blood and oxygen mixture exits therefrom through outlet ends of said tubes;

a flow guide member disposed about said first chamber adjacent said outlet ends of said tubes for directing the blood foam in a predetermined direction;

defoamer means, disposed in flow communication with said first chamber, for defoaming the blood foam after it exits from said tubes; and means for collecting the now oxygenated and defoamed blood.

4. A blood oxygenator according to claim 3 wherein each said oxygenator tube has a generally elliptical cross-section.

5. A blood oxygenator according to claim 3 or 4 further including means disposed between said flow guide member, and said first chamber adjacent said outlets of said tubes for encouraging the further oxygenation of said blood.

6. A blood oxygenator according to claim 5 wherein said oxygenating encouraging means comprises reticulated polyurethane foam.

7. A blood oxygenator according to claim 3 further including means for flowing a heat transfer fluid through said first chamber, exterior to said oxygenator tubes, such that the temperature of the blood flowing through said tubes can be regulated.

8. A blood oxygenator according to claim 3 further including a second chamber circumferentially surrounding said first chamber and providing a housing for said defoamer means and said first chamber.

9. The oxygenator according to claim 3 wherein said flow guide member is joined to said first chamber adjacent said outlet ends of said tubes and further including means for further oxygenating the blood sandwiched between said flow guide member and said first chamber.

10. The oxygenator according to claim 9 wherein said further oxygenating means comprises a ring of foam-like material.

11. A blood oxygenator comprising:

a first generally cylindrical chamber having a plurality of oxygenator tubes disposed therein, each said tube having an inlet adjacent a first end thereof and an outlet adjacent a second end thereof and a generally elliptical cross-section, said tubes arranged such that the elongated axis of each said tube is generally perpendicular to the radius of said first chamber, and further so as to form an annular array defining a central, open space extending from one end of said first chamber to the other;

a blood-oxygen mixing manifold joined to said first chamber adjacent the inlets of said tubes, and manifold having a blood inlet and an oxygen gas inlet, said manifold configured to mix said blood and oxygen and direct the mixture through said tubes, said mixture forming a blood foam as it flows out the outlets of said tubes;

means disposed about said first chamber adjacent the outlets of said tubes for encouraging the further oxygenation of said blood;

directing means located adjacent the outlets of said tubes for directing said blood foam through said oxygenating encouraging means;

defoamer means, located downstream of said oxygenating encouraging means, for defoaming said blood foam;

means for filtering said blood subsequent to it having been oxygenated;

a second chamber circumferentially disposed about said defoamer means and defining a housing; and means for removing the now oxygenated, filtered and defoamed blood from the oxygenator.

12. A blood oxygenator according to claim 11 wherein said oxygenating encouraging means is sandwiched between said directing means and said first chamber.

13. A blood oxygenator according to claim 11 or 12 wherein said oxygenating encouraging means comprises a ring of reticulated polyurethane foam.

14. A blood oxygenator according to claim 11 further including means for flowing a heat transfer fluid through said first chamber, exterior to said oxygenator tubes, such that the temperature of the blood flowing through said tubes can be regulated.

15. The oxygenator according to claim 11 further including means disposed in said control open space for spacing and positioning said tubes.

16. A blood oxygenator comprising:

a first generally cylindrical chamber having a plurality of oxygenator tubes disposed therein in a predetermined, generally annular array so as to define a central open space extending from one end of said first chamber to the other end thereof, each said tube having an elongated cross-section and positioned in said first chamber such that the elongated axis of each said tube is generally perpendicular to the radius of said first chamber, a base header plate and a top header plate joined to said chamber and securing said tubes in said predetermined array, and means for introducing a heat transfer fluid into said first chamber and removing the same therefrom;

mixing means for introducing a mixture of blood and oxygen bubbles into said oxygenator tubes, said mixing means joined to said first chamber adjacent said base header plate such that the blood and oxygen mixture flows through said tubes and exits therefrom adjacent said top header plate in the form of a blood foam;

a section of foam-like material for encouraging the further oxygenation of said blood disposed adjacent said top header plate;

flow guide means disposed adjacent said top header plate for directing substantially all said blood foam through said section of foam-like material;

defoamer means for defoaming the blood after it has flowed through said section of foam-like material;

means for collecting the blood after it has been defoamed; and blood outlet means for removing the now oxygenated and defoamed blood from the oxygenator.

17. A blood oxygenator according to claim 16 wherein each said oxygenator tube has a generally elliptical cross-section.

18. A blood oxygenator according to claim 16 further including a second chamber circumferentially disposed about said defoamer means.

19. A blood oxygenator comprising:

a first generally cylindrical chamber having a plurality of oxygenator tubes disposed therein in a predetermined generally annular array so as to define a central open space extending from one end of said first chamber to the other end thereof, each said tube having a generally elliptical cross-section with the elongated axis of each said tube generally perpendicular to the radius of said first chamber, a base header plate and a top header plate joined to said chamber and securing said tubes in said predetermined array, and means for introducing a heat transfer fluid into said first chamber and removing the same therefrom;

mixing means for introducing a mixture of blood and oxygen bubbles into said oxygenator tubes, said mixing means joined to said first chamber adjacent said base header plate such that the blood and oxygen mixture flows through said tubes where the blood is oxygenated and exits therefrom adjacent said top header plate in the form of a blood foam;

a ring of foam-like material for encouraging the further oxygenation of said blood disposed adjacent said top header plate;

defoamer means for deforming the blood after it has flowed through said ring;

a support member disposed about said defoamer means;

filter means disposed about said support member;

a second chamber disposed about said filter means and forming an exterior housing; and means for collecting the now oxygenated, filtered and defoamed blood.

* * * * *